United States Patent [19]

Friese et al.

[11] Patent Number: 5,310,575
[45] Date of Patent: May 10, 1994

[54] METHOD OF MAKING A POROUS CERAMIC PROTECTIVE LAYER ON AN ELECTRODE OF AN ELECTROCHEMICAL SENSOR FOR EXPOSURE TO HOT GAS

[75] Inventors: Karl-Hermann Friese, Leonberg; Hans-Martin Wiedenmann, Stuttgart; Eva Söll, Frankfurt, all of Fed. Rep. of Germany

[73] Assignee: Robert Bosch GmbH, Stuttgart, Fed. Rep. of Germany

[21] Appl. No.: 869,893

[22] Filed: Apr. 15, 1992

Related U.S. Application Data

[63] Continuation of Ser. No. 477,982, May 3, 1990, abandoned.

[30] Foreign Application Priority Data

Nov. 3, 1987 [DE] Fed. Rep. of Germany ....... 3737215

[51] Int. Cl.$^5$ .............................................. B05D 5/12
[52] U.S. Cl. .............................. 427/126.3; 427/126.4; 501/105; 204/429
[58] Field of Search .............. 204/424, 425, 426, 428, 204/429; 427/126.1, 126.3, 126.4; 501/135, 105

[56] References Cited

U.S. PATENT DOCUMENTS

| | | | |
|---|---|---|---|
| 3,935,089 | 1/1976 | Togawa et al. | 204/429 |
| 4,199,425 | 4/1980 | Sinkevitch | 204/429 |
| 4,225,634 | 9/1980 | Tanaka et al. | 204/429 X |
| 4,265,930 | 5/1981 | Shinohara et al. | 204/429 X |
| 4,296,148 | 10/1981 | Friese | 204/426 X |
| 4,402,820 | 9/1983 | Sano et al. | 204/429 X |
| 4,537,865 | 8/1985 | Okabe et al. | 501/135 |
| 4,584,086 | 4/1986 | Hayakawa et al. | 204/429 |
| 4,642,174 | 2/1987 | Shibata | 204/429 X |
| 4,859,307 | 8/1989 | Nishizawa et al. | 204/429 X |
| 4,915,814 | 4/1990 | Harada et al. | 204/429 X |

*Primary Examiner*—Nam X. Nguyen
*Attorney, Agent, or Firm*—Frishauf, Holtz, Goodman & Woodward

[57] ABSTRACT

An electrochemical measurement sensor for determining the oxygen content in gases, in particular in exhaust gases from internal combustion engines, having a solid electrolyte of stabilized zirconium dioxide and/or other oxygen ion-conductive oxides and at least one electrode on the side of the solid electrolyte exposed to the gas which is to be measured, is proposed, the electrode or electrodes containing, if desired, a ceramic support structure, and the electrode or electrodes exposed to the gas, which is to be measured, being covered by a porous ceramic protective layer of an $Al_2O_3$ and/or Mg spinel ($MgO.Al_2O_3$) matrix with preferably metastable $ZrO_2$ particles incorporated therein.

The use of an $Al_2O_3ZrO_2$ mixed oxide, which is preferably obtained by coprecipitation or by combination of suspensions of separately precipitated components or by spray-calcination of a combined solution of salts of the components and which may, if desired, contain a stabilizer for the $ZrO_2$, such as, for example, $Y_2O_3$, for forming the protective layer makes it possible, surprisingly, to form a firmly adhering, sintering-on protective layer which has a relatively narrow pore size distribution and which allows the best possible gas access to the outer electrode of the measurement sensor. The use of the $Al_2O_3/ZrO_2$ mixed-oxide powder also achieves very extensive balancing of the hitherto observed mismatch of mechanical stresses and layer strengths on the one hand and the desired porosity and sensor control position on the other hand.

8 Claims, 1 Drawing Sheet

FIG. 1
FIG. 2
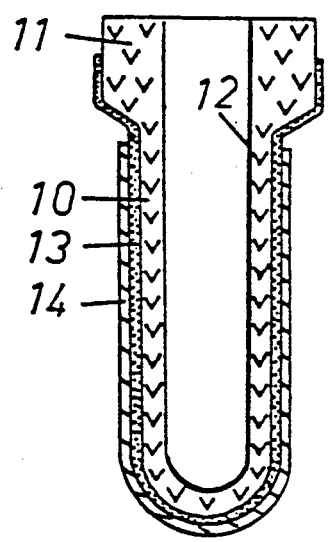
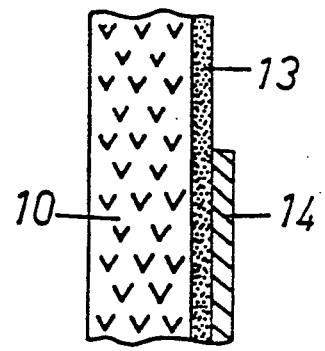

METHOD OF MAKING A POROUS CERAMIC PROTECTIVE LAYER ON AN ELECTRODE OF AN ELECTROCHEMICAL SENSOR FOR EXPOSURE TO HOT GAS

This application is a continuation of U.S. patent application Ser. No. 07/477,982, filed May 3, 1990 abandoned.

STATE OF THE ART

It is generally known, for example from German Offenlegungsschrift 2,711,880 and German Patent Specifications 2,852,647 and 2,913,633, to apply a porous ceramic protective layer to the electrode, which is exposed to the gas to be measured, in electrochemical measurement sensors. In the process known from German Patent Specification 2,852,647, the porous covering layer is applied to the electrode layer before sintering or before a heat treatment, during which sintering processes take place in the electrode layer, whereupon the layer system produced is then sintered together with the solid electrolyte, on which the layer system is located. Moreover, a remarkable improvement in the electrode activity is achieved in this co-sintering process.

Hitherto, $Al_2O_3$ covering layers or Mg spinel (MgO.$Al_2O_3$) covering layers without a dispersion-strengthener have been used in practice, even though, apart from these covering layers, those of stabilized zirconium dioxide, pure $ZrO_2$, zirconium silicate and titanium dioxide individually or as a mixture with one another are also described in German Patent Specification 2,852,647.

It is also generally known that zirconium dioxide occurs in various crystal forms, of which the monoclinic form, the tetragonal form and the cubic form are the most important. The problem with ceramic mouldings made from $ZrO_2$ is that the tetragonal form is metastable and comparatively easily undergoes a transition to the more stable monoclinic form. This can cause serious disadvantages in mouldings of $ZrO_2$ ceramics, which are exposed to thermal and/or corrosive stresses, for example those which are used for the production of electrochemical measurement sensors, since the mechanical properties of the solid ceramic bodies can suffer as a result of the irreversible transition from the metastable tetragonal form to the monoclinic form. In order to improve the mechanical properties of electrochemical measurement sensors based on $ZrO_2$ ceramics, it is known from U.S. Pat. No. 4,221,650 to use solid electrolyte mouldings of at least partially stabilized cubic $ZrO_2$ with a crystalline, aluminium-containing oxide dispersed therein.

Ceramic mouldings of high fracture toughness and a process for producing these are also known from German Patent Specification 2,549,652, which process comprises mixing a ceramic material forming a matrix and a ceramic incorporation material, dispersible therein, with one another, drying the mixture as appropriate, pressing it to give a moulding and then sintering the latter. The ceramic material forming a matrix can, for example, consist of $Al_2O_3$ and the incorporation material can consist of unstabilized $ZrO_2$ particles, the $ZrO_2$ content in the matrix advantageously being about 8 to 25% by volume.

A disadvantage of the covering layers hitherto used in electrochemical measurement sensors, in particular covering layers of pure $Al_2O_3$ or pure Mg spinel, is that they readily lead to considerable mechanical stresses in the composite probe block/covering layer system and hence to adhesion and strength problems. This is caused by differences in the shrinkage behavior during sintering and/or in the thermal expansion of probe block and covering layer. Corresponding problems can arise in the case of planar sensor elements, for example those of the type known from European Patents 0,162,603, 0,133,820, 0,125,069 and 0,168,938.

ADVANTAGES OF THE INVENTION

As compared with the hitherto disclosed protective layers of known electrochemical measurement sensors, a ceramic protective layer according to the invention exhibits the following advantageous properties:

The use of $Al_2O_3/ZrO_2$ mixed oxides, optionally containing additives of at least one other oxygen-ion-conductive oxide, which are obtained by co-precipitation or by combination of suspensions of separately precipitated hydroxides or by spray-calcination of a combined solution of Al and Zr salts and which may, optionally, contain a stabilizer for the $ZrO_2$, such as, for example, $Y_2O_3$, and may optionally contain a catalytically active material as further mentioned below, for forming the protective layer makes it possible, surprisingly, to form a firmly adhering, sintering-on protective layer having a relatively narrow pore size distribution. The relatively homogeneous porosity of the protective layer here allows the best possible gas access to the outer electrode of the measurement sensor. The use of the $Al_2O_3/ZrO_2$ mixed-oxide powder also achieves very extensive balancing of the hitherto observed mismatch of mechanical stresses and layer strengths on the one hand and the desired porosity and control position on the other hand.

Very obviously, metastable $ZrO_2$ particles incorporated into the $Al_2O_3$ matrix, in particular $\alpha$-$Al_2O_3$ matrix, can, by phase transformation, cause microcracks which absorb the energy of the mechanical stresses arising and hence have a positive influence on the strength of the bond between, for example, the probe block and the protective layer. However, even the coefficient of thermal expansion of the incorporated, optionally stabilized $ZrO_2$ particles, deviating from the coefficient of thermal expansion of the $Al_2O_3$ matrix, also leads to structural strains on cooling after the sintering process and hence to a strengthening of the porous protective layer.

The measurement sensors made by a process according to the invention may be of a kind having a tubular probe block or planar measurement sensors. These include, for example, also limiting-current sensors and limiting-current probes, for example such as are described in German Patent Applications P 37 28 618.8-52 and P 37 28 289.1-52.

It has proved to be advantageous for producing the protective layer to use an $Al_2O_3/ZrO_2$ mixed-oxide powder, with an optionally stabilized $ZrO_2$ component, of narrow particle size distribution. In an advantageous manner, the mixed-oxide powders can contain up to 50% by volume of optionally stabilized $ZrO_2$ powder. The use of mixed-oxide powders with 85 to 60% by volume of $Al_2O_3$ and 15 to 40% by volume of optionally stabilized $ZrO_2$ has also proved to be particularly advantageous. The $Al_2O_3$ can here be replaced wholly or partially by Mg spinel, the thermal properties of which are very similar to those of $\alpha$-$Al_2O_3$.

According to a further, particularly advantageous embodiment of the invention, comparatively small proportions of a catalytically active material, which allows the thermal/chemical equilibrium in the exhaust gas from an internal combustion engine to be established, are added to the mixed oxide, in order to obtain a control position which is as close as possible to $\lambda=1$.

In an advantageous manner, Pt powders and Pt alloy powders can be used. In an advantageous manner, they can be added in quantities from 0.05 to 5% by volume, in particular 0.1 to 1% by volume. For example, the addition of a Pt powder having a specific surface area of $\geq 10$ m$^2$/g has proved to be particularly advantageous. In addition, the incorporation of such catalytically active materials can contribute to the overall strength of the protective layer by the quasiplastic behavior under thermal stress.

The Al$_2$O$_3$/ZrO$_2$ mixed powders which can be used for producing measurement sensors according to the invention can be prepared in various ways by methods known per se.

For example, a suitable preparation process for the powder mixtures, which can be used according to the invention comprises hydrolizing solutions of aluminium oxychloride and zirconium oxychloride (ZrOCl$_2$.8 H$_2$O), if appropriate with an addition of YCl$_3$ or another suitable chloride, separating off the hydroxide mixture obtained, drying it, calcining it and grinding it. In place of chlorides, oxalates and alkoxides can also be used, for example. Another suitable preparation process comprises producing the mixed oxides by a combination of Al hydroxide and Zr hydroxide suspensions, which are produced separately by precipitation processes, and subsequent calcination. Moreover, a further suitable process comprises obtaining the mixed oxides, starting from a mixture of a suspension of $\alpha$-Al$_2$O$_3$ or $\gamma$-Al$_2$O$_3$ and a suspension of Zr hydroxide, by drying an Al$_2$O$_3$/Zr hydroxide mixture separated off from the mixture, calcining it and grinding it.

Finally, it is also possible, for example, to combine an Al$_2$O$_3$ suspension with a zironcium oxychloride solution and to hydrolyse the zirconium oxychloride in the mixture obtained to give zirconium hydroxide, to separate off the resulting mixture of Al$_2$O$_3$ and Zr hydroxide and to dry it, to calcine it and to grind it. In place of the Al$_2$O$_3$ suspension, an Mg spinel suspension can also be used in an advantageous manner. Furthermore, for example, the method known from U.S. Pat. No. 4,537,865 can also be used in an advantageous manner if a corresponding Al salt is used in place of a Ba, Sr, Ca or Mg salt. In all cases, the stabilizer precursor compounds such as, for example, YCl$_3$ can be added. The mixed-oxide powders having the desired ratios of Al$_2$O$_3$ and ZrO$_2$, Al$_2$O$_3$, Mg spinel and ZrO$_2$ as well as Mg spinel and ZrO$_2$ can be prepared by all the methods.

The protective layers can be applied as ceramic slips to the electrodes by known methods, for example by dipping, spraying, printing and the like, and, after a drying process, be sintered or resintered together with the probe block or the planar sensor element.

In an advantageous manner, the procedure is such that an approximately 50 to 200 $\mu$m thick layer is applied to the electrode or electrodes or also to major areas of the probe block or of the planar sensor element, the whole is dried at temperatures in the range from 60 to 150° C. for about 0.5 to 2 hours and then sintered or resintered at temperatures in the range from 1350 to 1500° C. for about 1 to 10 hours, depending on whether unsintered, presintered or fully sintered electrolyte bodies are used in the form of probe blocks or ceramic foils.

If appropriate, the protective layers can also be applied as powders, for example by the plasma-spraying technique, to the electrode areas of a probe block or of a planar sensor element built up from foils, it being possible for the latter in turn to be unsintered, presintered or fully sintered.

BRIEF DESCRIPTION OF THE DRAWINGS

The drawings serve for a more detailed explanation of the invention. In the drawings FIG. 1 shows the head of an electrochemical measurement sensor, in section, and FIG. 2 shows a portion of the measurement sensor according to FIG. 1 in an enlarged representation.

DETAILED DESCRIPTION OF THE DRAWINGS

The measurement sensor head consists of a tube 10, closed at one end, of a solid electrolyte, for example stabilized zirconium dioxide, the open end 11 of which has an increased wall thickness. The inner electrode 12, for example of 60% by volume of a palladium-platinum alloy with 20% by volume of platinum and 40% by volume of stabilized zirconium dioxide, is located on the inner wall of the tube 10 in the air reference channel. The outer electrode exposed to the gas being measured and consisting, for example, of 60% by volume of platinumrhodium with 20% by volume of rhodium and 40% by volume of stabilized zirconium dioxide is located on the outer wall of the tube 10, with the porous ceramic protect layer 14 on top. The measuring sensor head shown is part of a conventional electrochemical measurement sensor, such as is described in more detail in principle in, for example, German Patent Specification 2,913,633.

EXAMPLES

Example 1

65 parts by weight of a mixture consisting of 60 parts by weight of $\alpha$-Al$_2$O$_3$ powder ($\geq 99\%$ Al$_2$O$_3$; specific surface area 10 m$^2$/g) and 40 parts by weight of ZrO$_2$ powder ($\geq 99\%$ ZrO$_2$; specific surface area 1.5 m$^2$/g), 36 parts by weight of water and 2 parts by weight of polyvinyl alcohol as a binder were ground for 6 hours in a Vibratom mill.

The dispersion obtained was applied by spraying in a layer thickness of about 150 $\mu$m to the part, provided with an electrode layer, of a presintered electrolyte body of a measurement sensor head of the type shown in FIGS. 1 and 2. The measurement sensor body was then resintered for about 3 hours at a temperature in the region of 1400° C.

A protective layer, largely free of mechanical strains, of homogeneous porosity and high layer strength was obtained in this way above the electrode exposed to the gas to be measured.

Example 2

The procedure described in Example 1 was repeated, but with the exception that this time a partially stabilized ZrO$_2$ powder (YSZ powder) with 2 mol % of Y$_2$O$_3$ and a specific surface area of $\approx 14$ m$^2$/g was used in place of the unstabilized ZrO$_2$ powder.

Example 3

The procedure described in Example 1 was repeated, but with the exception that this time an $Al_2O_3/ZrO_2$ mixed powder, obtained by coprecipitation, with 40% by weight of $ZrO_2$ and a specific surface area of $\approx 10$ $m^2/g$ was used in place of the mixture of $Al_2O_3$ powder and $ZrO_2$ powder.

Example 4

The following were ground together in a centrifugal ball mill:

100 parts by weight of a mixed-oxide powder consisting of 60 parts by weight of $Al_2O_3$ and 40 parts by weight of $ZrO_2$, as described in Example 3, 8 parts by weight of polyvinyl butyral as a binder, 4 parts by weight of dibutyl phthalate as a plasticizer and 50 parts by weight of butylcarbitol as a solvent.

The duration of grinding was 2 hours.

The paste obtained was printed by screen-printing onto the electrodes of planar sensor elements, such as are described in German Patent Applications P 37 28 618.8-52 and P 37 28 289.1-52, in the unsintered state of the latter.

After drying-on, sintering was carried out for 2 hours at a temperature in the region of 1400° C.

Protective layers, very largely free of mechanical strains, of homogeneous porosity were again obtained above the electrodes.

Example 5

In order to demonstrate the dependence of the quality of the layer bond of the porous protective layer and the solid electrolyte body coated with electrodes on the $ZrO_2$ content of the protective layer, protective layers of printing pastes of varying $ZrO_2$ content were printed onto the electrodes of probe blocks of the type known from German Patent Specification 2,852,647. Four of the printing pastes used were prepared by the procedure described in Example 4, starting from $Al_2O_3/ZrO_2$ mixed-oxide powders obtained by coprecipitation. The printing pastes contained the binder, plasticizer and solvent quantities indicated in Example 4. The following results were obtained:

| $Al_2O_3$ % by weight | $ZrO_2$ % by weight | Quality of the layer bond (relative units) |
|---|---|---|
| 100 | — | 30 |
| 95 | 5 | 48 |
| 80 | 20 | 62 |
| 70 | 30 | 69 |
| 60 | 40 | 78 |

The results obtained show that the quality of the layer bond increases with increasing $ZrO_2$ content.

Example 6

An $Al_2O_3/ZrO_2$ suspension with an organic binder/solvent system consisting of:

40 parts by weight of terpinol and 60 parts by weight of benzyl alcohol with an addition of 4–10% by weight of ethylcellulose was applied by dip-coating or spraying to the presintered solid electrolyte body, provided with electrode layers of a sensor element of the type described in German Patent Specification 2,852,647. The suspension was obtained by stirring 65 parts by weight of an $Al_2O_3/ZrO_2$ mixture as described in Example 3 and 35 parts by weight of the solvent system for 15 minutes in a conventional agitator.

After the application of the suspension, drying was carried out for ½ hour at a temperature in the region of 100° C. The product was then resintered at a temperature in the region of 1400° C.

A protective layer, very largely free of mechanical strains, of homogeneous porosity and high layer strength was again obtained.

We claim:

1. A method of making a porous ceramic protective layer on at least one electrode of an electrochemical measurement sensor for exposure to hot gas which is to be measured by said sensor for determining the oxygen content in the gas, said sensor having a solid electrolyte of oxygen-ion-conducting oxide composed predominantly of stabilized zirconium dioxide and having at least one said electrode on one side of the solid electrolyte, said method comprising the steps of:

co-precipitating the hydroxides corresponding to an aluminum oxide matrix material and a solid electrolyte oxide, said matrix material being selected from the group consisting of aluminum oxide, magnesium spinel, and mixtures of aluminum oxide and magnesium spinel, and said solid electrolyte oxide consisting essentially of stabilized zirconium dioxide, said hydroxides being co-precipitated in a proportion that will produce a content of from 15 to 50% by volume of said solid electrolyte oxide in a calcined precipitate;

then calcining the precipitated hydroxides to form a mixed oxide powder, and applying said mixed oxide powder on said at least one electrode of said sensor.

2. The method of claim 1, wherein there is added, the mixed oxide powder before application on said at least one electrode ofs aid sensor, a catalytically active material for establishing a thermal equilibrium between said hot gas and said solid electrolyte oxide.

3. The method of claim 1 wherein the calcination takes place after the application of the oxide powder on said at least one electrode.

4. The method of claim 1, wherein the calcination takes place before the oxide powder is applied as a layer on said at least one electrode.

5. A method of producing a porous ceramic layer on at least one electrode of an electrochemical measurement sensor for exposure to hot gas which is to be measured by said sensor for determining the oxygen content in the gas, said sensor having a solid electrolyte of oxygen-ion-conducting oxide composed predominantly of stabilized zirconium dioxide and having at least one said gas-exposed electrode on one side of the solid electrolyte, said method comprising the steps of:

separately precipitating hydroxides corresponding respectively to an aluminum oxide matrix material and to a solid electrolyte oxide, said matrix material being selected from the group consisting of aluminum oxide, magnesium spinel, and mixtures of aluminum oxide and magnesium spinel, and said solid electrolyte oxide consisting essentially of stabilized zirconium dioxide;

mixing said separately precipitated hydroxides in a proportion such that said solid electrolyte oxide will constitute between 15 and 50% by volume of mixed oxides producible from the hydroxide mixture;

calcining the precipitated hydroxides to form a mixed oxide powder, and applying said mixed oxide powder on said at least one electrode of said sensor.

6. The method of claim 5, in which the calcining step is performed after the mixing of said precipitated hydroxides and before the step of applying said oxide powder on said at least one electrode.

7. The method of claim 5, wherein the calcining step takes place after the application of mixed precipitated hydroxides on said at least one electrode.

8. The method of producing a porous ceramic layer on at least one electrode of an electrochemical measurement sensor for exposure to hot gas which is to be measured by said sensor for determining the oxygen content in the gas, said sensor having a solid electrolyte of oxygen-ion-conducting oxide composed predominantly of stabilized zirconium dioxide and having at least one said electrode on one side of the solid electrolyte, said method comprising the steps of:

spray-calcinating a common solution of salts corresponding to the respective oxides of an aluminum matrix material and of an oxygen--ion-conductive solid electrolyte to obtain a mixed oxide powder, said matrix material being selected from the group consisting of aluminum oxide, magnesium spinel, and mixtures of aluminum oxide and magnesium spinel, and said solid electrolyte oxide consisting essentially of stabilized zirconium dioxide and being present in a proportion by which said solid electrolyte will constitute between 15 and 50% by volume of said mixed oxide powder and applying said mixed oxide powder as a porous ceramic layer on said at least one electrode.

* * * * *